(12) United States Patent
Toimela et al.

(10) Patent No.: US 11,969,244 B2
(45) Date of Patent: Apr. 30, 2024

(54) TRACKING PIECES FOR TRACKING MOVEMENTS OF HARD TISSUE OF A JAW

(71) Applicant: PLANMECA OY, Helsinki (FI)

(72) Inventors: Lasse Toimela, Helsinki (FI); Kustaa Nyholm, Helsinki (FI)

( * ) Notice: Subject to any disclaimer, the term of this patent is extended or adjusted under 35 U.S.C. 154(b) by 1283 days.

(21) Appl. No.: 16/472,370

(22) PCT Filed: Dec. 14, 2017

(86) PCT No.: PCT/FI2017/050890
§ 371 (c)(1),
(2) Date: Jun. 21, 2019

(87) PCT Pub. No.: WO2018/115576
PCT Pub. Date: Jun. 28, 2018

(65) Prior Publication Data
US 2019/0358008 A1 Nov. 28, 2019

(30) Foreign Application Priority Data
Dec. 23, 2016 (FI) ...................................... 20166026

(51) Int. Cl.
| | | |
|---|---|---|
| *A61B 5/11* | (2006.01) | |
| *A61B 5/00* | (2006.01) | |
| *A61B 6/00* | (2006.01) | |
| *A61B 6/03* | (2006.01) | |
| *A61B 6/14* | (2006.01) | |
| *A61B 6/40* | (2024.01) | |

(Continued)

(52) U.S. Cl.
CPC .......... *A61B 5/1127* (2013.01); *A61B 5/4542* (2013.01); *A61B 5/682* (2013.01); *A61B 6/032* (2013.01); *A61B 6/14* (2013.01); *A61B 6/4085* (2013.01); *A61B 6/4441* (2013.01); *A61B 6/505* (2013.01); *A61B 90/39* (2016.02); *A61C 19/045* (2013.01); *B33Y 50/00* (2014.12); *B33Y 80/00* (2014.12); *G06F 30/00* (2020.01); *A61B 2090/3916* (2016.02); *A61B 2090/3945* (2016.02); *A61B 2090/3966* (2016.02); *A61C 19/04* (2013.01)

(58) Field of Classification Search
CPC ......... A61B 6/14; A61B 5/682; A61B 5/4542; A61C 19/04
See application file for complete search history.

(56) References Cited

U.S. PATENT DOCUMENTS

| | | |
|---|---|---|
| 4,836,778 A | 6/1989 | Baumrind et al. |
| 4,859,181 A | 8/1989 | Neumeyer |

(Continued)

FOREIGN PATENT DOCUMENTS

| | | |
|---|---|---|
| WO | 2013175018 A1 | 11/2013 |
| WO | 2016090476 A1 | 6/2016 |
| WO | 2016142264 A1 | 9/2016 |

*Primary Examiner* — Angela M Hoffa
*Assistant Examiner* — Younhee Choi
(74) *Attorney, Agent, or Firm* — Lippes Mathias LLP

(57) ABSTRACT

The invention relates to tracking pieces (110) used in the context of tracking movements of hard tissue of a jaw. According to the invention, a tracking piece (110) to be used in such context is designed to be patient-specific by including in the design of the tracking piece (110) a surface model representing a part of a person's intraoral anatomy, which surface model is generated based on imaging results acquired by imaging the anatomy.

8 Claims, 4 Drawing Sheets

(51) Int. Cl.
*A61B 6/50* (2024.01)
*A61B 90/00* (2016.01)
*A61C 19/04* (2006.01)
*A61C 19/045* (2006.01)
*B33Y 50/00* (2015.01)
*B33Y 80/00* (2015.01)
*G06F 30/00* (2020.01)

(56) References Cited

U.S. PATENT DOCUMENTS

| | | | |
|---|---|---|---|
| 9,999,487 B2 | 6/2018 | Kusch et al. | |
| 2008/0064008 A1* | 3/2008 | Schmitt | A61C 13/0004 382/128 |
| 2009/0305185 A1 | 12/2009 | Lauren | |
| 2010/0198566 A1 | 8/2010 | Lauren | |
| 2013/0157218 A1 | 6/2013 | Brunner et al. | |
| 2015/0132716 A1 | 5/2015 | Kusch et al. | |
| 2015/0238345 A1* | 8/2015 | Decker | A61C 5/007 382/128 |
| 2016/0128624 A1 | 5/2016 | Matt | |
| 2016/0157967 A1* | 6/2016 | Kim | A61C 8/005 433/201.1 |
| 2016/0166174 A1* | 6/2016 | Daon | A61B 1/00 433/27 |
| 2016/0262711 A1 | 9/2016 | Nyholm et al. | |

\* cited by examiner

US 11,969,244 B2

TRACKING PIECES FOR TRACKING MOVEMENTS OF HARD TISSUE OF A JAW

FIELD OF INVENTION

The invention relates to tracking pieces used in the context of tracking movements of hard tissue of a jaw, particularly to generating digital models of such tracking pieces, to manufacturing such tracking pieces, and to software products as well as arrangements relating to the designing and manufacturing such tracking pieces.

BACKGROUND OF INVENTION

Concerning diagnosis and treatment of temporomandibular disorders, various methods and devices have been used relating to recording jaw movements. Resolving a pose and motion of a lower jaw bone relative to an upper law bone is difficult because visual observation of anatomies located behind a layer or soft tissue is not possible. Various systems such as ones employing mechanical, electronic, ultrasonic, electromagnetic and optical techniques have been used in connection with recording movements of a human jaw. One typical solution includes attaching physical markers, which can also be called surrogate objects, to both maxilla and mandible, and recording their respective relative movement. Typically the markers are elongated pieces extending out of a person's mouth and their movement, induced by movement of a person's jaw, is observed and recorded. This movement can then be visualized on a display, such as applied to a digital model of a related anatomy.

Regardless the technology used in such procedures, the work-flow involved is often time-consuming and laborious as it may include using separate apparatus and operations performed individually and separate from each other. These operations may include attaching markers to the anatomy, generating jaw movements, detecting and recording the movements of the markers, and generating a model which visualizes the jaw movements, which visualization may then be shown on a display. For one, in case acquiring imaging results relating to movements of the markers and visualization of the jaw movements are separate process and it is realized only afterwards that additional movement information would have been needed or at least be desirable to have, to enhance the digital model of the jaw movement, generating such additional information will not be possible until the next time one will be able to harness the same person with the markers and detect and record the marker movements anew.

The known processes of attaching the surrogate objects to a person's anatomy include using adhesives or other attaching methods. The overall process necessitates resolving in some way the relative spatial positions of the surrogate objects and the anatomy. Any calibration system is prone to inaccuracies and, concerning many of the prior art arrangements, it is practically impossible to repeat in a subsequent study exactly the same relative positioning of the surrogate objects and the anatomy.

Examples of prior art relating to tracking jaw movements include systems described in patent publications U.S. Pat. Nos. 4,836,778, 4,859,181, US 2013/0157218 and WO 2013/0175018.

BRIEF DESCRIPTION OF INVENTION

The following presents a simplified summary of the invention in order to provide a basic understanding of some aspects or objects of the invention. This summary is not intended to identify key or critical elements of the invention or to delineate the scope of the invention.

An object of the present invention is to provide novel means for tracking movements of hard tissue of a jaw of a person by using a novel type of tracking piece, the novelty being based on a novel method for designing such tracking pieces. This novel designing method is based on making use of a digital model generated from imaging results of a person's anatomy, which makes it possible to manufacture patient-specific tracking pieces.

Various aspects of the invention comprise methods, an apparatus, a tracking piece, an arrangement and a computer program, which are characterized by what is stated in the attached independent claims.

Further aspects of the invention are disclosed in the attached dependent claims as well as in the more detailed description below.

One advantage provided by one or more aspect of the invention includes being able to track movements of hard tissue of a jaw by using a patient-specific tracking piece which forms a perfectly fitting shell on top of a person's anatomy, especially on top of at least part of teeth of the lower law. Due to this perfect fit, no additional adhesives or only a minimal amount of adhesives is required to firmly fit the tracking piece to the anatomy. When the tracking piece according to the invention will be exactly in a known connection with the anatomy, no separate calibration step after attaching the tracking piece to the person's anatomy is needed. Further, the same tracking piece can be used several times without any additional calibration phase. Thus, tracking the hard tissue movements can be carried out fluently with just a single physical tracking piece and the same tracking piece may be used several times, even over a long period of time.

BRIEF DESCRIPTION OF FIGURES

The following FIGS. present some aspects of various embodiments of the invention.

DETAILED DESCRIPTION OF INVENTION

The following are examples of embodiments of the invention. Although the specification may refer to "an", "one", or "some" embodiment(s) in various locations, this does not necessarily mean that each such reference is to the same embodiment(s) or that a feature of an embodiment only applies to that particular single embodiment. Individual features of various embodiments may be combined or left out to provide embodiments not necessarily literally disclosed in detail.

Figure 1:
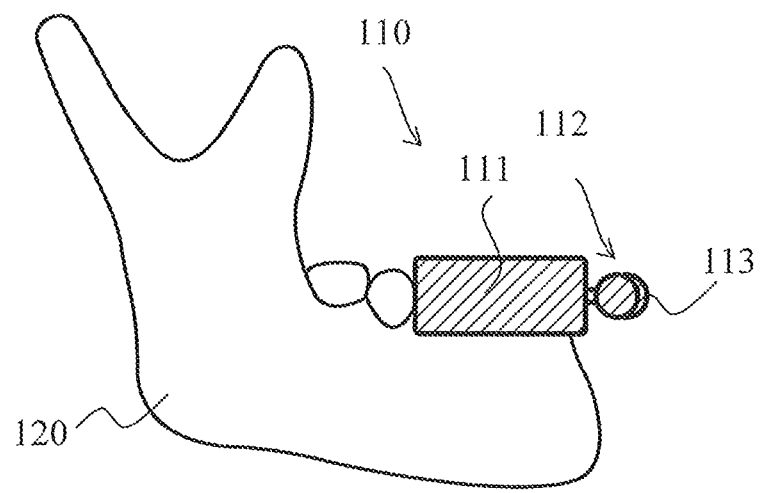
FIG. 1 shows a tracking piece attached to a lower jaw of a person.

FIG. 1 shows as a side view a physical tracking piece (110) attached to the lower jaw (120) of a person. The tracking piece (110) comprises a splint part (111) and at least one protruding part (112). The protruding part (112) is configured to extend out of the person's mouth. The protruding part (112) of FIG. 1 further comprises at least one tracking marker (113). The tracking marker (113) may be integrated with the protruding part (112) or it may be configured to be attachable, possibly detachably attachable to the protruding part (112). The tracking marker (113) may be arranged to reflect or emit at least one wavelength, it may e.g. comprise at least one LED, at least one IR reflecting object or at least one light reflecting object. A tracking marker (113) may be radio-opaque or it may include a radio-opaque part.

The physical tracking piece (110) according to FIG. 1 can be designed and manufactured as a patient-specific tracking piece via first generating a digital model of a tracking piece (110) which as for its splint part (111) is designed based on digital surface data (3D surface model) of a person's true anatomy. The image data to generate the surface data may be acquired by imaging an impression of the anatomy or by directly imaging the person's anatomy. The inner surface of the splint part (111) to meet the intraoral anatomy can then be designed to be a perfect fit to the surface of the person's anatomy. The overall shape of the splint part (111), i.e. a digital model including not only the surface conforming to the person's anatomy but also the other surfaces of the splint part (111), can be designed more freely.

The overall designing process of the tracking piece (110) can further include designing a digital model of at least one protruding part (112), which is to be attached or integrated with to the splint part (111), and/or designing to the splint part (111) at least one connection structure for at least one protruding part (112). The process may thus comprise, for example, designing a digital model of the splint part (111) having one surface area conforming to the surface of a particular person's intra-oral anatomy and combining that model with one representing a surface of at least one protruding part (112), and optionally also structures of or relating to at least one tracking marker (113), to form a digital model of the tracking piece (110).

Figure 2:
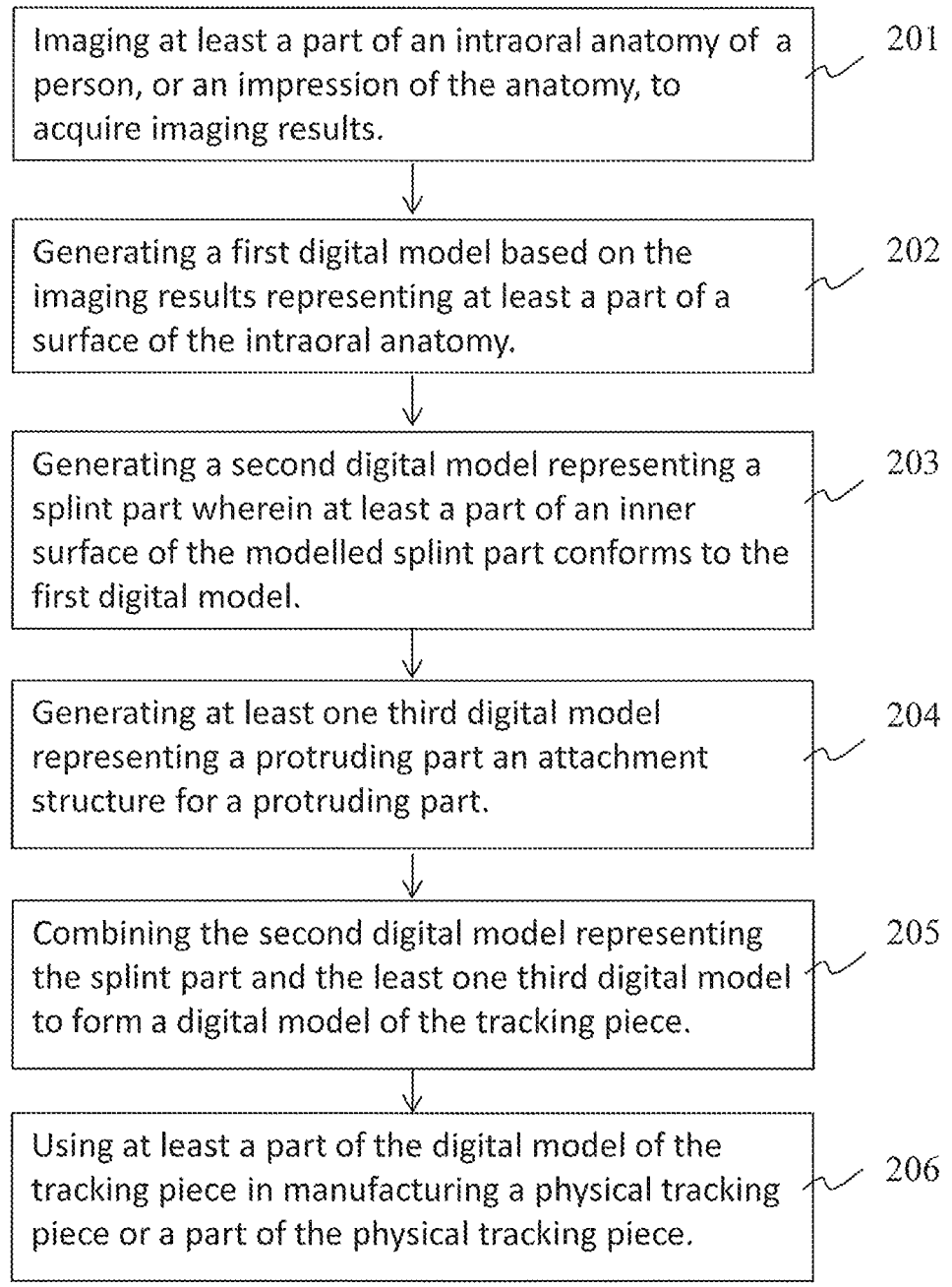
FIG. 2 shows a flew chart of a designing and subsequent manufacturing process according to one embodiment of the invention.

FIG. 2 is a flow chart illustrating an example of steps related to generating a digital model of a tracking piece.

FIG. 2 further shows a subsequent step of manufacturing a physical tracking piece, which comprises the splint part and further the at least one protruding part or at least one connection structure for at least one protruding part.

Concerning the process shown in FIG. 2 in step (201) at least a part of an intraoral anatomy of a person, or an impression of the anatomy, is imaged to acquire imaging results. The anatomy may include, as examples, at least a part of teeth, tooth surfaces, gingival or other fine details of the person's intraoral anatomy. Acquiring said imaging results may comprise using an optical intra-oral surface scanning device or a CT or CBCT imaging device.

In step (202), a first digital model is generated based on the imaging results, which model represents at least a part of a surface of the person's intraoral anatomy.

In step (203), a second digital model is generated which represents the splint part (111) and comprises at least a part of said fist digital model. One way to describe this step is that the model of the splint part (111) is generated by taking the surface model of the anatomy as a starting data to form at least part of an inner, or bottom surface of the splint part, and then "building up" the actual overall shape of the model of the splint part (111) on top of the modelled surface of the anatomy.

In step (204), at least one third digital model is generated which represents at least one protruding part (112) or an attachment structure for at least one protruding part (112).

In step (205), the second digital model representing the splint part (112) and the at least one third digital model are combined to form a digital model of the tracking piece (110).

The method of generating the digital model of a tracking piece is presented in FIG. 2 as including certain specific individual steps (201)-(205) but, obviously, not all of the steps need to be performed separately. As an example, the steps (203)-(205) as disclosed above may be described comprising "generating a digital model of the tracking piece (110) which comprises a second digital model representing the splint part (111) and at least a part of said first digital model, and a third digital model as combined to the second digital model, the third digital model representing at least one protruding part (112) or an attachment structure for the at least one protruding part (112)".

The model of the protruding part (112) may optionally include a model of at least one tracking marker (113) or a model of an attachment structure for the at least one tracking marker (113). Obviously, again, the model of the protruding part (112) may be generated as directly including any such model or models or such model or models can be designed separately and then be combined with the model at the protruding part (112).

In other words, while one or several models of tracking markers (113) may be integrated with the model of the protruding part (112) or may be designed to be attachable to the protruding part (112), "the third digital model" may comprise not only the protruding part (112) hut also at least one tracking marker (113) or an attachment structure therefor.

The digital model of the tracking piece (110) or the part of the tracking piece may be stored for later use, such as for manufacturing the physical patient-specific tracking piece (110) or the part of the patient-specific tracking piece.

Hence, according to one aspect of the invention, step (205) of FIG. 2 is followed by step (206) in which at least a part of the generated digital model of the tracking piece (110) is used in manufacturing a physical tracking piece (110), or a part of a physical tracking piece. To put this in other words, the digital model of the tracking piece (110) forms the base data for a subsequent manufacturing of the physical tracking piece (110) or a part of the physical tracking piece.

The physical tracking piece (110) can be manufactured in a CAD/CAM arrangement including apparatus like a 3D printer or a milling cutter.

The physical tracking piece (110) can be designed and manufactured in such a way that the location of the at least one tracking marker (113) in relation to the digital surface model of the person's intra-oral anatomy, used for designing the splint part (111) of the tracking piece (110), is known.

On the other hand, depending on the design, a part or parts of the tracking piece (110) whose location in relation to the particular digital surface model of the person's intra-oral anatomy is to be known may also be some other structure of the tracking piece (110) than a tracking marker (113) as shown in FIG. 1.

According to one aspect of the invention, an arrangement to implement the invention may comprise a CT or a CBCT imaging device, a computer comprising software for implementing at least some of the process steps as described in reference to FIG. 2 and related text passages above, and e.g. an additive manufacturing machine or a milling machine to manufacture the physical object designed according to the invention.

Consequently, one embodiment of the invention may comprise a computer program embodied on a computer-readable storage medium, the computer program comprising program code to control and execute at least some of the steps the method described in connection with FIG. 2, such as at least part of the steps (201)-(205) discussed in reference to FIG. 2.

Figure 3:
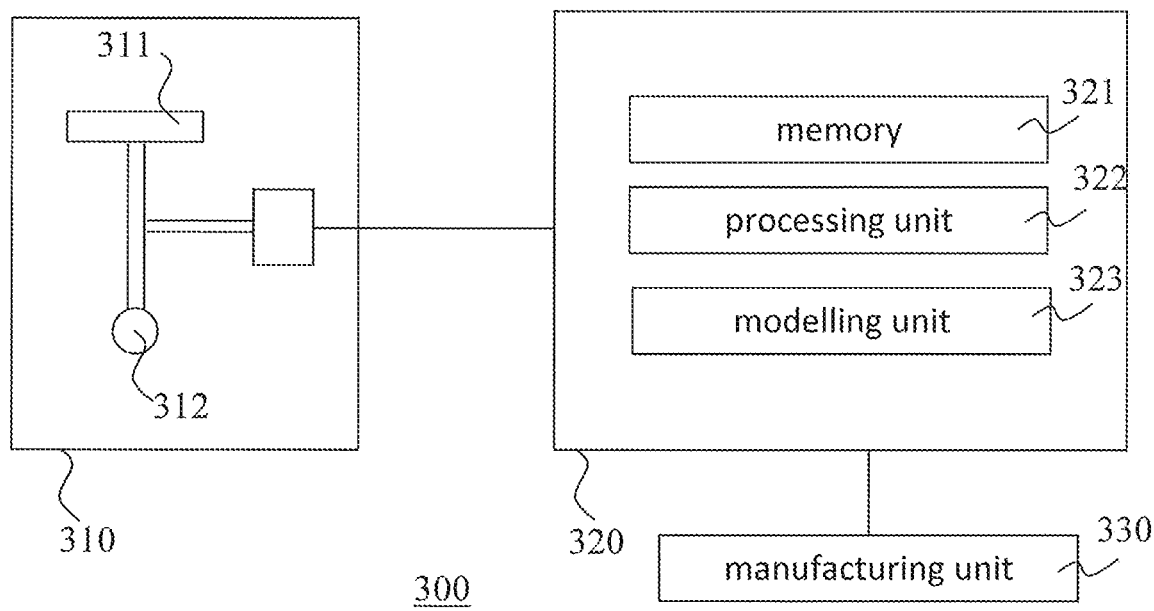
FIG. 3 shows a block diagram of parts of one preferred arrangement according to the invention.

A general architecture of one arrangement (300) to implement the invention, shown in FIG. 3, comprises an imaging device (310), which may be a CBCT scanner comprising a detector (311) and a radiation source (312), and a data processing system (320) which may comprise a memory (321) and a scanning results processing unit (322). The scanning results processing unit (322) may be configured to numerically reconstruct scanning results to produce what is termed a digital volume or volumetric data composed of three dimensional pixels, i.e. voxels, representing the anatomy that has been scanned. The data processing system (320) may further comprise a modelling unit (223) configured to interact with the data generated by the processing unit (322) to generate digital models of scanned anatomies, and of the tracking piece (110). The data processing system (320) may be configured to also record such models in the memory (321).

One embodiment of the invention such as one shown FIG. 3 may further comprise a manufacturing unit (333), for example a 3D printer or a milling cutter configured to generate a physical tracking piece (110) or a part of the physical tracking piece (110) from a digital model or a part of the digital model of the tracking piece (110) created by the modelling unit (323).

Figure 4:
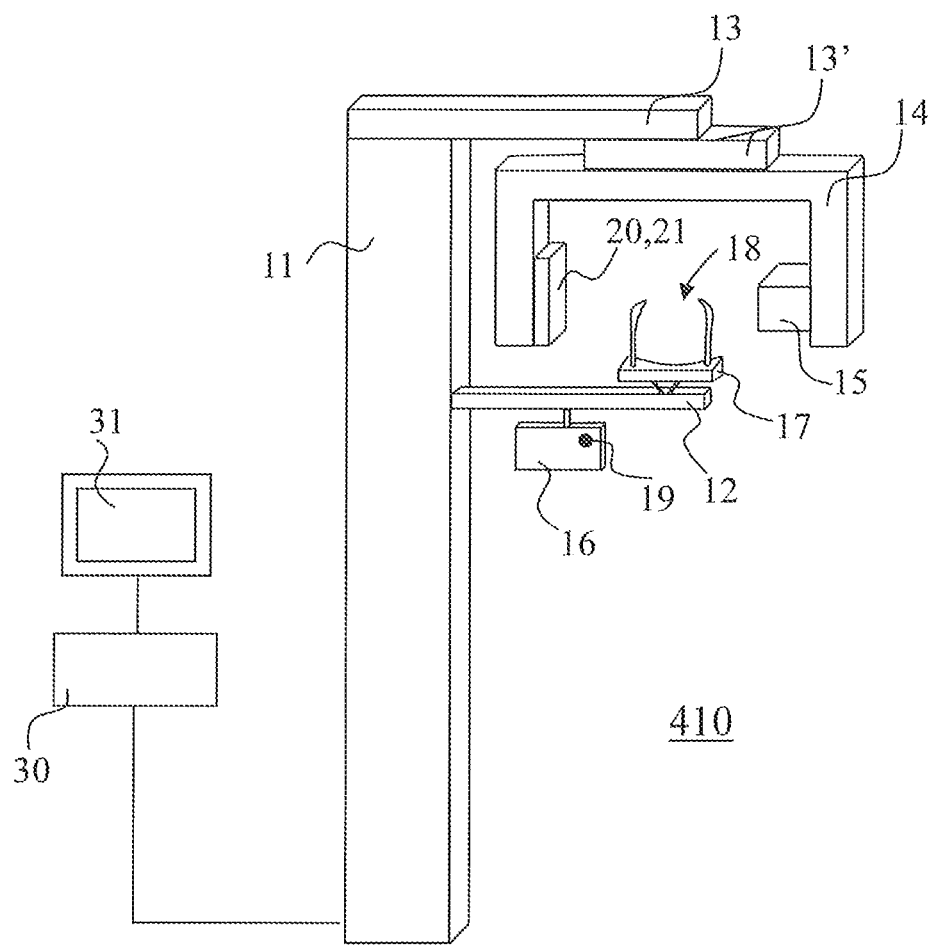
FIG. 4 shows an example of an imaging apparatus applicable for use in the context of the invention.

While the apparatus for acquiring imaging results for a surface model of an anatomy may be an optical intraoral scanner like the one commercially distributed under a registered trademark Planmeca PlanScan, an example of a CBCT apparatus applicable for use in connection with the invention is shown in FIG. 4. The imaging apparatus (410) of FIG. 4 includes a vertical support construction (11) from which horizontally extends an arm (12) supporting a patient support means (17) and an arm part (13, 13') which supports an arm part (14) supporting imaging means of the apparatus. The arm part (14) supporting the imaging means is arranged rotatable, as may be the arm part (13, 13') which supports the arm part (14) supporting imaging means. (FIG. 4 shows an apparatus in which the arm part (13, 13') which supports the arm part (14) supporting imaging means consist of two parts out which at least the second one (13') may be arranged rotatable, but those two parts (13, 13') may be arranged to form just a single monolithic arm part as well.) The imaging means of the apparatus include an x-ray source (15) and a receiver of x-ray image information (21) arranged at a distance from each other on the arm part (14) supporting the imaging means. The imaging means are located with respect to the patient support means (17) such that an imaging station (18) is created within an area between the x-ray source (15) and the receiver of x-ray image information (21) such that a beam generated by the x-ray source (15) can be directed through said imaging station (18) towards the receiver of x-ray image information (21). The apparatus includes control means out of which FIG. 4 shows a user interface (16) arranged to the arm (12) supporting a patient support means (17), which may include an operation mode selection means (19). The receiver of x-ray image information (21) can be arranged as part of a receiver module of image information (20), i.e. a detector module (20) which in addition to the receiver of x-ray image information (21) may comprise one or more optical cameras (to be discussed below). A means for processing image information is arranged to the computer (30), which is also arranged in an operational connection with a display (31). The user interface (16) may be equipped with a display, too, and there may be a display arranged to some other structure of the imaging apparatus as well.

In case an optical intraoral scanner is used for generating a model of an intraoral surface yet one wishes to be able to display movements of also other hard tissue of a jaw than that visible to an optical scanner, like movements of a jaw bone as a whole, one needs to combine such surface model with a model including the same anatomy generated by some other applicable imaging device such a CBCT scanner discussed above. In case a CBCT or other applicable scan of the person's anatomy is already made, the data of such scan can be used to generate a desired intraoral surface model and no additional optical scanning and, thus, also no such combining needs to be done at all.

Figure 5:
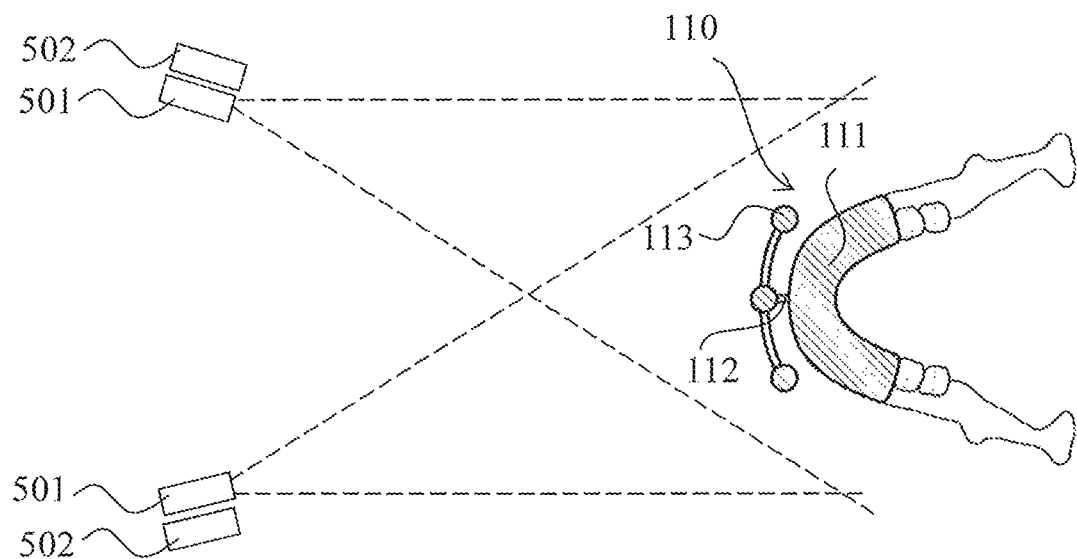
FIG. 5 shows as an example one principled arrangement for motion tracking imaging in which a tracking piece is attached to a mandible, in the field of view of two cameras.

FIG. 5 shows an arrangement for detecting jaw motion according one system applicable for use in the context of the invention. The arrangement includes two optical cameras (501) arranged at a distance from each other and aimed to photograph a person's head. A tracking piece (110) according to the invention is attached to the person so that when moving one's jaw, the tracking piece (110) follows the movements of the jaw. The arrangement of FIG. 5 also includes light sources (502) arranged at close proximity of the cameras (22) and to emit light essentially in a direction at which the cameras (22) are aimed. An x-ray imaging apparatus such as shown in FIG. 4 may be configured to further comprise an arrangement as shown in FIG. 5, such as by including optical cameras to a detector module as disclosed above.

The arrangement according to FIG. 5 for acquiring information for generating a digital model depicting motion of cranial hard tissue as discussed above is based on using two cameras, but arrangements based on using some other number of cameras can be used for that purpose just as well.

One aspect of the invention is thus a method for tracking movements of hard tissue of a person's jaw, comprising detecting movements of at least marker attached to a person's anatomy and mapping those movements to a person's anatomy, wherein said at least one marker is part of a tracking piece (110) as manufactured as discussed above and the detecting of the movements includes detecting movements of the tracking piece (110) while being attached in a form-fitting manner to an anatomy corresponding the surface based on which said tracking piece (110) has been designed.

Figure 6:
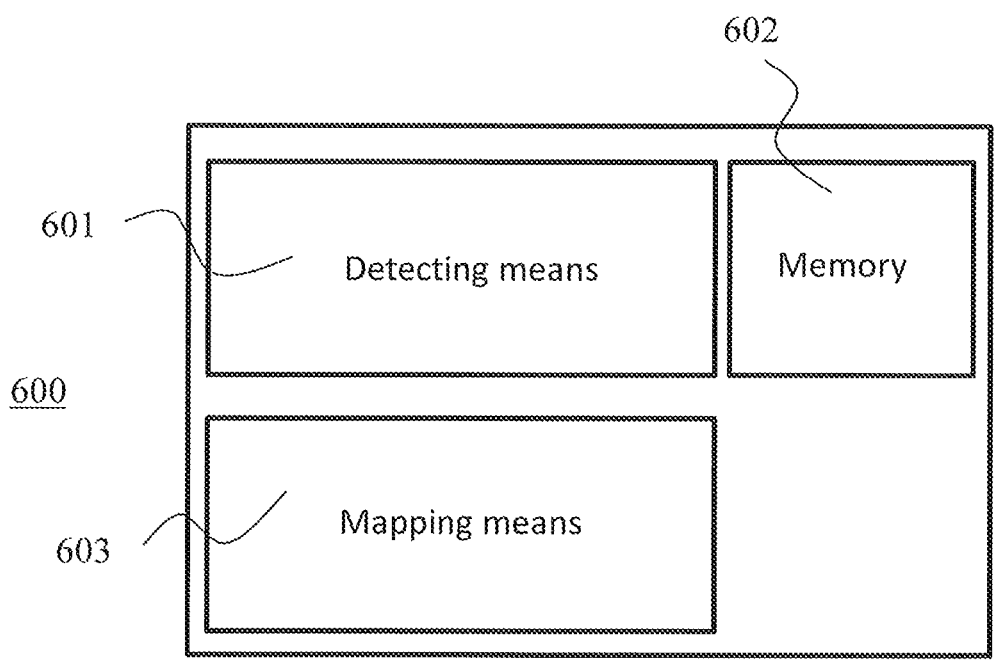
FIG. 6 shows a principled tracking system for detecting movements of surrogate objects and for modelling movements of hard tissue of a jaw.

FIG. 6 shows a principled system for detecting and modelling jaw motion, a tracking system (600), which may be implemented as part of an imaging device (610) of FIG. 4. The tracking system (600) is configured to resolve movements of the jaw by detecting movements of e.g. at least one protruding part (112) or tracking marker (113) of the tracking piece (110) and by mapping said movements to a virtual model of an anatomy. The tracking system (600) may thus comprise a detecting means (601) for detecting movements of the at least one protruding part (112) or tracking marker (113). The detecting means (601) may comprise an arrangement of FIG. 5 for detecting movements (of at least a part of) the physical tracking piece (110) when being attached to a person's anatomy, the physical tracking piece (110) being designed and manufactured as form-fitting to the anatomy. The tracking system (600) may further comprise a memory (602) for storing the detected movements. For being able to display not only the movements of the tracking piece (110) but also those of the actual anatomy, or just those of the anatomy, the tracking system (600) of FIG. 6 comprises a mapping means (603) for mapping the movements of the tracking piece (110) to at least part of the imaging results of the person's intra-oral anatomy, i.e. to at least part of the modelled surface of the anatomy which was used for manufacturing the physical patient-specific tracking piece (110).

It will be obvious to a person skilled in the art that, as the technology advances, the inventive concept disclosed herein can be implemented in various ways. The invention and its embodiments are not limited to the examples described above but may vary within the scope of the attached claims.

The invention claimed is:

1. A method for tracking a jaw movement with a tracking piece manufactured according to the following process, the tracking piece being configured to be attached to a person's anatomy and to follow movements of a jaw of a person with no separate calibration step being required, said tracking piece comprising a splint part and at least one protruding part, or the splint part and an attachment structure for the at least one protruding part, the method comprising:
   imaging at least a part of an intraoral anatomy of the person or an impression of said intraoral anatomy to acquire imaging results;
   generating based on said imaging results a first digital model representing a surface of said intraoral anatomy;
   generating a digital model of the tracking piece comprising
      i) a second digital model representing the splint part and comprising said first digital model and
      ii) a third digital model combined to the second digital model, the third digital model representing the at least one protruding part or the attachment structure for the at least one protruding part;
   manufacturing the tracking piece based on the digital model of the tracking piece specific to the person;
   attaching the tracking piece to the person's anatomy; and
   tracking the tracking piece to follow movement of the jaw of the person.

2. The method according to claim 1, further comprising generating a fourth digital model representing a tracking marker or an attachment structure for the tracking marker and combining said fourth digital model to the third digital model representing the at least one protruding part.

3. The method according to claim 2, wherein acquiring said imaging results comprises using an optical intra-oral surface scanning device or a CT or CBCT imaging device.

4. The method according to claim 1, comprising manufacturing said manufactured tracking piece using an additive manufacturing machine, a 3D printer, or a milling cutter.

5. The method according to claim 4, wherein the manufactured tracking piece is configured to form a fitted shell on top of at least part of teeth of the person's lower jaw.

6. The method according to claim 1, wherein at least one tracking marker is integrated with the protruding part or is removably attached to the protruding part and wherein said at least one tracking marker integrated with or attached to the at least one protruding part further comprises a means for reflecting or emitting at least one wave length.

7. The method according to claim 1, wherein the tracking piece further comprises at least one marker.

8. The method according to claim 1, wherein the second digital model represents at least a bottom surface of the splint part.

* * * * *